United States Patent [19]

Eilon et al.

[11] Patent Number: 4,927,965
[45] Date of Patent: May 22, 1990

[54] N-(N-SUCCINYL-L-LEUCYL)AGMATINE, RELATED COMPOUNDS AND USE IN PHARMACOLOGY

[75] Inventors: Gabriel F. Eilon, Wyndmoor; Wayne J. Thompson, Green Lane, both of Pa.

[73] Assignee: Merck & Co., Inc., Rahway, N.J.

[21] Appl. No.: 266,609

[22] Filed: Nov. 3, 1988

[51] Int. Cl.$^5$ ............... C07C 129/12; C07C 125/065
[52] U.S. Cl. ................... 562/560; 560/137; 560/145; 560/159; 560/168; 560/169; 562/555
[58] Field of Search ............... 562/560, 555; 560/137, 560/145, 159, 168, 169

[56] References Cited

U.S. PATENT DOCUMENTS 4,228,184 10/1980 Ondetti ............... 562/560
4,418,075 11/1983 Tamai ............... 424/278

OTHER PUBLICATIONS

Osteolytic Bone Metastases in Breast Carcinoma Pathogenesis, Morbidity and Bisphosphonate Treatment, Elte et al., Pergamon Prfess (1986), pp. 493–500.
Biochemical and Histomorphometric Characterization of a Rat Model for Humoral Hypercalcemia of Malignancy, Insogna et al., Endocrinology, vol. 114, No. 3, pp. 888–896.
The Hypercalcemic Rat Leydig Cell Tumor–a Model of the Humoral Hypercalcemia of Malginance, Sica et al., Calc. Tiss. Internatl., (1983), 35, pp. 287–293.
Comparison of Two Parenteral Diphosphonates in Hypercalcemia of Malignancy, A. Jung, Amer. J. of Med., vol. 72, pp. 221–226.
Effects of Disodium Dichloromethylene Diphosphonate on Hypercalcemia Produced by Bone Metastases, Chapuy et al., J. Clin. Invest., vol. 65, (1980), 1243–1247.
The Effects of Dichloromethylene Diphosphonate on Hypercalcemia and Other Parameters of the Humoral Hypercalcemia of Malig. in the Rat Leydig Cell Tumor, Martodam et al., Calc. Tiss. Internatl., (1983), 35: 512–519.
L-Trans-Epoxysuccinyl-Leucylamido (4-Guanidino)-Butane(E-64) and its Analogues as Inhibitors of Cysteine Proteinases Including Cathespsins B, H, and L. Barrett et al., Biochem. J. (1982), 201, pp. 189–198.
In Vivo and In Vitro Evidence for the Involvement of Cysteine Proteinases in Bone Resorption, Delaisse et al., Biochem. and Biophysical Res. Comm., vol. 125, No. 2, 1984, pp. 441–447.
The Cysteine Protease Inhibitor, E-64, Stimulates the Polarization and Locomotor Responses of Endothelial Cells to Wounding, Eilon et al., The Jornl. of Phar. & Exp. Therp., vol. 24, No. 1, pp. 361–367 (1988).

Primary Examiner—Michael L. Shippen
Attorney, Agent, or Firm—John W. Harbour; Charles M. Caruso

[57] ABSTRACT

Compounds having the formula:

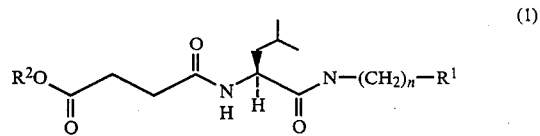

(1)

wherein $R^1$ is $-NH(C=O)OR^5$, $-NH(C=NH)NH_2$ or $-NH(C=N-NO_2)HN_2$; $R^2$ is hydrogen, $C_{1-8}$alkyl or $C_{6-8}$aryl; n is 2 to 6; and $R^5$ is hydrogen, $C_{1-8}$alkyl, $C_{6-8}$aryl, or $C_{7-8}$alkaryl; are disclosed in addition to methods to employ such compounds to induce migration of endothelial cells into denuded areas of vessel lining and to treat malignant hypercalcemia.

5 Claims, No Drawings

N-(N-SUCCINYL-L-LEUCYL)AGMATINE, RELATED COMPOUNDS AND USE IN PHARMACOLOGY

BACKGROUND OF THE INVENTION

A class of compounds that show promise by acting as class specific inhibitors of cysteine proteinase are L-trans-epoxysuccinyl peptides. One such peptide is the compoudn L-trans-epoxysuccinyl-L-leucylamido (e-guanidino) butane. This compound was shown to inhibit papain with the disappearance of the thiol group of papain and to inhibit cathepsin B, L, and H. By contrast, the serine proteinases and the indicated that L-trans-epoxysuccinyl-L-leucylamido (e-guanidino) butane inactivates cathepsin B and L by a stoichiometric reaction with the cystein residue essential for catalytic activity [Barrett et al., Biochem, J. (1982) 201, 189–198]. The kinetics of inhibition also show that the action of L-trans-epxoysuccinyl-L-leucylamido (e-guanidino) butane is not competitive with substrate and that the binding is irreversible by a covalent reaction at the active site. The inhibitor is selective due to the affinity of the inhibitors to the appropriate peptide components (di-peptide) for the specificity site of the proteinases.

Certain epoxysuccinyl amino acid derivatives, including L-trans-epoxysuccinyl-L-leucylamido (e-guanidino) butane, (known as E-64), are shown in U.S. Pat. No. 4,418,075 and the art cited therein. The compounds of U.S. Patent 4,418,075, however, are taught to be inhibitors of calcium-activated neutral thio protease useful in the treatment of muscular dystrophy. These same compounds are shown and by R. N. Mascardo and G. F. Eilon, J. Pharm. Exper. Therap., 244, 361–367, 1988, to be effective to promote endothelial cell migration to wounded areas.

Although epxoy succinyl amino acid derivatives are useful to achieve effects as taught, further compounds to achieve the same effects are desired, especially compounds which do not contain epoxy groups. Epoxy groups are alkylating agents and associated with cellulor toxicity.

Thus, it is a purpose of the present invention to produce N-(N-succinyl-L-leucyl)agmatine and related compounds.

It is further a purpose of the present invention to demonstrate the usefulness of such compounds in applications for which the epoxysuccinyl amino acids described above are known to be effective.

SUMMARY OF THE INVENTION

Briefly, the present invention is directed to compounds having the formula:

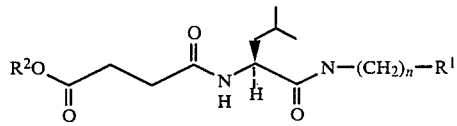
(1)

wherein $R^1$ is $-NH(C=O)OR^5$, $-NH(C=NH)NH_1$ or $-NH(C=N-NO_2)NH_2$; $R^2$ is hydrogen, $C_{1-8}$ alkyl or $C_{6-8}$aryl; n is 2 to 6; and $R^5$ is hydrogen, $C_{1-8}$ alky, $C_{6-8}$aryl, or $C_{7-8}$alkaryl. There are further described methods to employ such compounds to induce migration of endothelia cells into wounded areas of vessel lining and to treat malignant hypercalcemia.

DETAILED DESCRIPTION OF THE INVENTION

One aspect of the invention can be readily understood by reference to the following flow sheet which exhibits the process for the synthesis of the active ingredient through certain intermediates. In another aspect of the invention, the active ingredient of Formula I is mixed with a non-toxic pharmaceutical carrier and divided into unit doses, each dose containing a vessel healing or bone disease treating amount of the active ingredient.

The therapeutic methods of the present invention comprises the administration of effective amounts of the active ingredient together with desired pharmaceutically acceptable diluents, adjuvants and carriers to an animal suffering from vessel damage or a bone disease. In the case of vessel damage, the unit dosage may be administered orally but is preferably administered intravenously in a continuous or periodic fashion. Daily dosage of active ingredient should range from about 1 to 500mg/kg of body weight of animal to be treated, and preferably from 10 to 50mg/kg of body weight. In the case of bone disease intravenous introduction may be employed but oral administration is the desired route for practice of the invention. Therein, unit dosage forms of compound of from 0.1 to 500 mg are periodically administered. Such unit dosage forms may be given to provide a daily dosage of from 1 to 500 mg/kg of body weight of the animal to be treated, preferrably from 10 to 50 mg/kg body weight.

FLOW SHEET

Flow Sheet

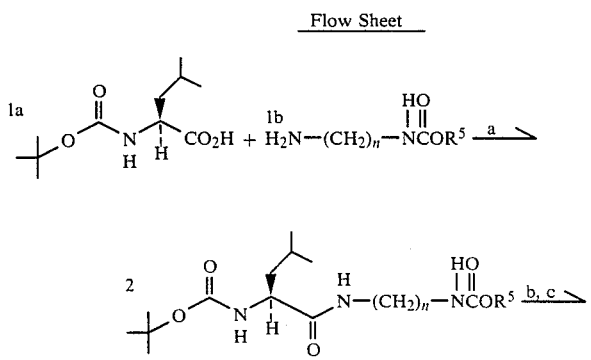

Flow Sheet

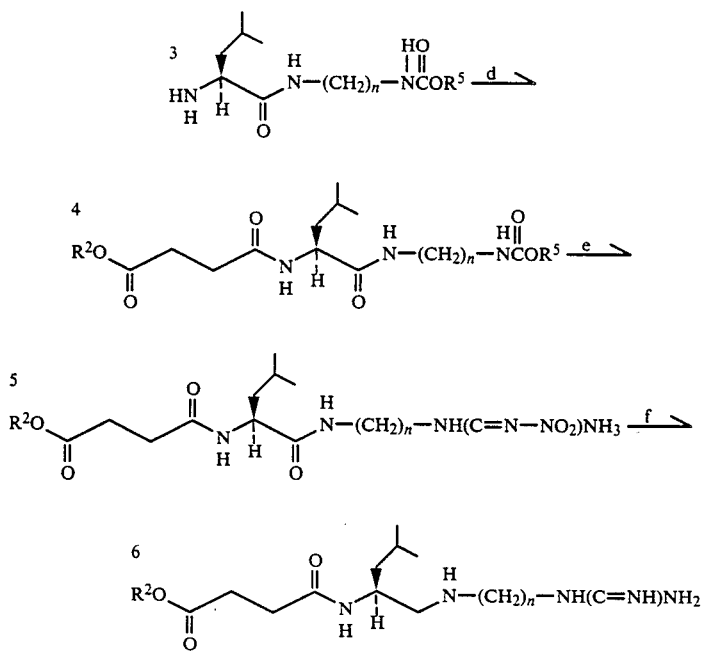

Referring to the flow sheet, compounds 1a and 1b are reacted, "a", at from 0° C. to room temperature in are reacted, "a", at from 0° C. to room temperature in isobutyl chloroformate, N-methylmorpholine and ethyl acetate to form N-(Boc-L-leucyl)-N'-carboxylate-1,4-diaminobutane, compoudn 2. Compound 2 is reacted, "b", with formic acid and "c" with NaOH to deprotect the amine group thereof and produce compoudn 3, N-(L-leucyl)-N'-carboxylate-1,4-diaminobutane. Compound 3 is actylated "d" to produce N-(succinyl-L-leucyl)-N'-carboxylate-1,4-diaminobutane, compound 4. Where $R^2$ of compound 4 is to be hydrogen, then acylation should be with succinic anhydride in $CH_2Cl_2$ and where $R^3$ is alkyl or aryl then acylation should be in monoalky succinoyl chloride or monoaryl succinoyl chloride in pyridine and $CH_2Cl_2$. Compuoind 4 is reacted "e" to N-[N-succinyl-L-leucyl]-N$^{(G)}$-nitroagmatine, compound 5 by nitreoguanylation. First an acetate salt is formed by dissolving compound 4 in EtOH, glacial AcOH and $H_2O$ and passing the solution over palladium under a hydrogen atmosphere. The salt is recovered, dissolved in EtOH and refluxed with $Et_3N$ and 3,5-dimethyl-1-nitroguanylpyrazole. Compound 5 is converted to active compound 6 i.e. N-(N-succinyl-L-leucyl)agmatine by saponification and reduction. Compound 5 is saponified in MeOH and KOH. Reduction is carried out by subsequently dissolving in EtOH, AcOH and $H_2O$ and passing over palladium under a hydrogen atmosphere.

The following examples are for illustrative purposes only and are not to be considered as limiting the invention in any way.

EXAMPLE 1

N-(N-Succinyl-L-leucyl)agmatine (SLA) was prepared from starting materials, Boc-L-leucine and N-carbobenoxy-1,4-diaminobutane in five steps. The preparation through step 2 making N-carbobenzoxy-N'-L-leucyl-1,4 diaminobutane is described by, K. Hanada, M. Tamai, S. Ohmura, J. Sawada, T. Seki and I. Tanaka, Agric. Biol. Chem., 43, 529–536, 1978.

STEP 1

N-(BOC-L-LEUCYL)-N'-CARBOBENZOXY-1,4-DIMAINOBUTANE, (INTER 1) FROM STARTING MATERIALS BY ACYLATION

A solution of 13 g (52.2 mmole) of Boc-L-leucine monohydrate in 200 mL of ethyl acetate was dried for 30 min over 2 g of anhydrous magnesium sulfate, then filtered and cooled in an ice-brine bath while stirring magnetically under nitrogen. To this solution was added 6.1 mL of N-methylmorpholine followed by 7.2 mL of isobutylchloroformate. After stirring for 20 min, a solution of 11.6 g of N-carbobenzoxy-1,4-diaminobutane [1] in 300 mL of ethyl acetate was added and the mixture allowed to warm to room temperature over 2 hrs. The resulting mixture was washed with three 200 mL portions of 0.5 M citric acid, 100 mL of dilute sodium bicarbonate, dried over anhydrous magnesium sulfate and concentrated under reduced pressure. The product, Inter 1, was purified by column chromatography on silica gel, eluting with 7/3 ethyl acetate/hexanes. Fractions containing product homogeneous by TLC were combined and concentrated to a white crystalline solid (15.2g 67%): mp 89-89.5° C., $^1$H-NMR (300 MHz, CDC13)δ0.92 (dd, 6H, J=2, 4Hz), 1.43 (s, 9H), 1.52 (m, 4H), 1.65 (m, 2H), 3.20 (m, 4H), 4.05 (m, 1H), 4.90 (m, 2H), 5.10 (s, 2H), 6.30 (br m, 1H) 7.35 (m, 5H).

STEP 2

N-CARBOBENZOXY-N'-L-LEUCYL-1,4-DIAMINOBUTANE (INTER 2) FROM INTER 1 UPON DEPROTECTION

A solution of 4.35 g (10 mmole) of Inter 1 in 90 mL of 98% formic acid was kept at room temperature for 3 hrs, then concentrated on the rotary evaporator keeping the bath temperature below 30° C. The resulting oil was taken up in 50 mL of diethyl ether and allowed to stand overnight in the refrigerator. The white solid was collected by filtration (2.48 g) and recrystallized from 100 mL of hot ethyl acetate. After drying under vacuum there was obtained 2.34g (61%) of colorless crystals: mp 102°–10° C., $[\alpha]^{20}_D+9.4$ (c=0.585, MeOH) The formate salt was dissolved in 20 mL of 0.5N NaOH and extracted with four 50 mL portions of CHCl$_3$. The combined chloroform extracts were washed with 50 mL of brine, dried over MgSO$_4$ and concentrated to give 2.12 g of the free based as a solid, Inter 2.

STEP 3

N-CARBOBENZOXY-N'-[N-(ETHYLSUCCINYL)-L-LEUCYL)-1,4-DIAMINOBUTANE (INTER 3) FROM INTER 2 BY ACYLATION

To an ice cooled, stirred solution of 2.12 g (6.32 mmole) of Inter. 2 in 20 mL of CH$_2$Cl$_2$ was added 1.0 mL of pyridine followed by 1.25 mL (8.85 mmole) of ethyl succinyl chloride. The mixture was allowed to warm to room temperature and stir for 1 hr, then diluted with 150 mL of CHCl$_3$, washed with 50 mL of 1N HCl, dried over MgSO$_4$ and concentrated. The product, Inter 3, was purified by column chromatography on silica gel, eluting with 1/19 MeOH/CHCl$_3$. The appropriate fractions were combined and concentrated to dryness affording 3.46 g of a white foam: $[\alpha]^{20}_D$ −24.14 (c=0.555, MeOH) $^1$H-NMR (300 MHz, CDCl$_3$)δ0.92 (t, 6H, J =6.8 Hz), 123 (t, 3H, J=7.0 Hz) 1.50 (br s, 4H), 1.55–1.80 (m, 3H), 2.4–2.8 (m, 4H), 3.1–3.3 (m, 4H), 4.11 (g, 2H J=7.0 Hz), 4,42 (m, 1H), 5.10 (S, 2H), 5.20 (t, 1H), 6.37 (d, 1H, 8.2 Hz), 6.79 (t, 1H), 7.34 (s, 5H).

STEP 4

N-[N-(ETHYL SUCCINYL)-L-LEUCYL]-N$^{(G)}$-NITROAGMATINE (INTER 4) FROM INTER 3 BY NITROGUANYLATION

A solution of 3.3 g (7.1 mmole) of Inter 3 in 50 mL of EtOH, 12 mL of glacial AcOH and 6 mL of H$_2$O was shaken with 0.3 g of 10% palladium on carbon (Engelhardt) under 50 psi of hydrogen of 3 hrs. The mixture was filtered, concentrated and dried under vacuum to give 3.5 g of the acetate salts as a foam. The crude acetate salt was dissolved in 100 mL of EtOH and warmed to reflux with 2.3 mL (9.25 mmole) of Et$_3$N and 1.75 g (9.5 mmole) of 3,5-dimethyl-l-nitroquanyl-pyrazole[2] for 5 hrs. After concentrating to dryness under reduced pressure, the residue was dissolved in 250 mL of ethyl acetate and washed with 200 mL of 1M citric acid, 100 mL of H$_2$O, dried (MgSO$_4$) and again concentrated to dryness. Column chromatography over a 3"×6" column of silica gel eluting first with 1 L of ethyl acetate, then 0.5 L of 1/9 acetone/ethyl acetate and finally 750 mL of 1/2 acetone/ethyl acetate gave 1.25 g of a colorless form after drying which was homogeneous by thin layer chromatography. $^1$H-NMR (300 MHz, CDCl$_3$) w 0.87 (d, 3H, J=6.4 Hz), 0.90 (d, 3H, J=6.4 Hz), 1.23 (t, 3H, J=7 Hz), 1.70 (br m, 7H), 2.5–2.8 (m, 4H), 3.2–3.5 (br m, 4H), 4.1 (g, 2h, J=7 Hz), 4.48, (br, s, 1H) 7.25 (br m, 1H), 7.45 (br m, 1H) 7.8 (br m, 2H), 8.6 (br m, 1H).

STEP 5

N-(N-SUCCINYL-L-LEUCYL-AGMATINE (SLA) FROM INTER 4 BY SAPONIFICATION AND REDUCTION

To an ice cooled, stirred solution of 1.25 g (3 mmole) of Inter 4 in 8 mL of MeOH was added 2.6 mL of 2N KOH. The mixture was allowed to warm and stir at room temperature for 4 hrs, then diluted with 40 mL of H$_2$O, neutralized with 8 mL of Dowex 50W (H$^+$ form-washed with distilled H$_2$O and MeOH until filtrate was colorless), filtered and concentrated to dryness under reduced pressure. The semi-solid mass was dissolved in 40 mL of EtOH, 4 mL AcOH and 4 mL of H$_2$O and shaken with 0.150 g of 10% palladium on carbon (Engelhardt) under 50 psi of hydrogen for 12 hr. The mixture was filtered, concentrated and dried under vacuum. The residue was titrated with 200 mL of CH$_3$CN and pulverized into a white solid. The solid was dried to constant weight under vacuum at 25° C. (1.15 g): Anal. Calcd. for C$_{15}$H$_{29}$N$_5$O$_4$0.5 AcOH·H$_2$O: C, 49.09; H, 8.49; N, 17.89. Found: C, 49.01; H, 8.45; N, 18.10. $^1$H-NMR (300 MHz, D$_2$O +TSP)δ0.89 (d, 3H, J=6.4 Hz), 0.93 (d, 3H, J=6.4 Hz), 1.6 (m, 7H, 1.95 (s, 1.5H), 2.5 (br s, 4H), 3.2 (br m, 4H), 4.22 (dd, 1H, J=4.0 and 6.0 Hz). $[\alpha]^{20}_d$−31.3 (c=0.502, 0.1 N HCl).

1. J. S. Rao, Hoppe-Seylers Z. Physiol. Chem., 349, 251 (1968).

2. A. F. S. A. Habeeb, pi Biochim. Biophys. Acta., 93, 533 (1964).

EXAMPLES 2-

These examples show the application of SLA in the healing of damaged vessel lining.

Bovine pulmonary artery cells were cultured on glass cover slips to confluency and wounded by scraping a 25–30 cell wide path off the cover slip as described by (Mascardo & Sherline, Diabetes 33:1099 1984). SLA and insulin were applied to wounded areas as show in Table 2. Changes in wound width were observed and recorded on video camera. Recorded images of the wound at 0,1,2,3, hours after denudation were analyzed. Results were expressed as the mean percent change in wound width.

MEANS CHANGES IN WOUND WIDTH (% ±S-E)

$$100 - \left( \frac{\text{wound width at time } M}{\text{wound width at time } O} \right) \times 100$$

TABLE 1

| | Healing of Wounded Vessel Lining | | | |
|---|---|---|---|---|
| | | Example | | |
| Time/ Treatment | C None | 2 1 uM SLA | 3 10 uM SLA | 4 1 uM Insulin |
| 0 hr | 0 | 0 | 0 | 0 |
| 1 hr | −1 + 0.5 | 13 + 1.0 | 16 + 1.0 | 14 + 2.0 |
| 2 Hr | 0 + 0.2 | 21 + 1.0 | 28 + 2.0 | 24 + 0.5 |
| 3 hr | 3 + 0.8 | 28 + 1.5 | 32 + 2.2 | 26 + 1.0 |

This data indicates that SLA has a chemokinetic effect on endothelial cells causing cells to migrate to 'wounded' areas in vitro. Insulin a know hormone to have endothelial wound healing properties shows a similar effect in this model. The indication that SLA affects migration of cells implies radical changes in adherence properties of the affected cells.

EXAMPLES 5 AND 6

These examples show the effect of SLA on malignant hypercalcemia.

A rat model that closely mimics the human syndrome of Humoral Hpercalcemia of Malignancy was described by Insogna et al, *Endocrinology* 114, 888-896 (1984). In this model a Rice 500 Leydig cell tumor is transplanted, tumor bearing animals are significantly hypercalcemic. Bone histomorphometry shows uncoupling of bone cell function in the tumor group with marked bone resorption and with marked suppression of bone formation. These findings exactly parallel those in human humoral hypercalcemia of malignancy.

Fisher 344 rats were transplanted with a Rice-500 Leydig tumor. On day 11 following the transplant, 40 mg/kg of SLA was administered orally. Serum Ca++ was monitored daily and a control group is compared to the treated group as shown in Table 2.

TABLE 2

Effect of SLA on Malignant Hypercalcemia

| Day | | | | |
|---|---|---|---|---|
| 11 | 12 | 13 | 14 | 15 |
| Example 5: CONTROL ANIMALS | | | | |
| 13.5 | 14.6 | 14.8 | 14.6 | 15.1 |
| 13.8 | 13.3 | 15.2 | 15.1 | 14.8 |
| 14.1 | 13.8 | 14.6 | 13.8 | 13.9 |
| 12.6 | 14.4 | 15.0 | 14.2 | 14.3 |
| 12.8 | 14.7 | 14.4 | 13.6 | 14.4 |
| 13.1 | 14.1 | 14.9 | 13.9 | 14.1 |
| 13.3 + 0.2 | 14.15 + 0.2 | 14.81 + 0.10 | 14.2 + 0.2 | 14.43 + 0.16 |
| Example 6: SLA-TEATMENT (40 mg/kg) | | | | |
| 12.8 | 10.1 | 11.6 | 11.8 | 12.6 |
| 12.7 | 9.7 | 11.2 | 12.2 | 13.1 |
| 13.3 | 10.3 | 10.8 | 12.1 | 13.2 |
| 12.9 | 9.6 | 10.4 | 11.7 | 13.4 |
| 13.4 | 9.9 | 10.4 | 11.5 | 13.3 |
| 13.1 | 9.7 | 10.9 | 12.0 | 13.0 |
| 13.03 + 0.10 | 9.88 + 0.1 | 10.75 + 0.2 | 11.88 + 0.09 | 13.1 + 0.10 |

What is claimed is:

1. Compounds having the formula:

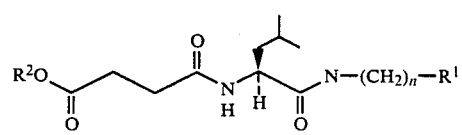

(1)

wherein $R^1$ is $-NH(C=O)OR^5$, $-NH(C=NH)NH_2$ or $-NH(C=N-NO_2)HN_2$; $R^2$ is hydrogen. $C_{1-8}$alkyl or $C_{6-8}$aryl; n is 2 to 6; and $R^5$ is hydrogen, $C_{1-8}$alkyl, $C_{6-8}$aryl, or $C_{7-8}$alkaryl.

2. The compound of claim 1 wherein $R^1$ is amino carbonyl benzoxy, $-NH(C=NH)NH_2$ or $-NH(C=N-NO_2)NH_2$.

3. The compound claim 1 wherein $R^2$ is hydrogen.

4. The compound of claim 1 wherein $R^2$ is hydrogen, and R1 is $-NH(C=NH)NH_2$.

5. The compound of claim 1 named N-(N-succinyl-L-leucyl)agmatine.

* * * * *